(12) United States Patent
Lee

(10) Patent No.: US 10,926,019 B2
(45) Date of Patent: Feb. 23, 2021

(54) GRADIENT DIALYSATE HEMODIAFILTRATION

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 103 days.

(21) Appl. No.: 16/431,935

(22) Filed: Jun. 5, 2019

(65) Prior Publication Data

US 2020/0384180 A1 Dec. 10, 2020

(51) Int. Cl.
*A61M 1/34* (2006.01)

(52) U.S. Cl.
CPC ........ *A61M 1/3455* (2013.01); *A61M 1/3406* (2014.02); *A61M 1/3413* (2013.01); *A61M 2205/3324* (2013.01); *A61M 2230/20* (2013.01)

(58) Field of Classification Search
CPC .............. A61M 1/3455; A61M 1/3413; A61M 1/3406; A61M 2202/0498; A61M 2205/3324; A61M 2230/20; A61M 2230/208; B01D 63/02
See application file for complete search history.

(56) References Cited

U.S. PATENT DOCUMENTS

| | | | |
|---|---|---|---|
| 3,463,728 A | 8/1969 | Kolobow et al. | |
| 4,212,744 A | 7/1980 | Oota | |
| 4,861,485 A | 8/1989 | Fecondini | |
| 5,075,003 A | 12/1991 | Aoyagi | |
| 5,194,157 A | 3/1993 | Ghezzi et al. | |
| 5,366,630 A | 11/1994 | Chevallet | |
| 5,578,223 A | 11/1996 | Bene et al. | |
| 5,660,722 A | 8/1997 | Nederlof | |
| 5,849,419 A | 12/1998 | Nederlof | |
| 5,919,369 A | 7/1999 | Ash | |
| 6,315,895 B1 | 11/2001 | Summerton et al. | |
| 6,561,996 B1 | 5/2003 | Gorsuch | |
| 6,561,997 B1 | 5/2003 | Weitzel et al. | |
| 6,635,179 B1 | 10/2003 | Summerton et al. | |

(Continued)

FOREIGN PATENT DOCUMENTS

| AT | 408955 B | 9/2001 |
|---|---|---|
| DE | 2851929 A1 | 4/1980 |

(Continued)

OTHER PUBLICATIONS

Etinger A, Kumar, Ackley W, et al: The effect of isohydric hemodialysis on the binding and removal of uremic retention solutes PLoS ONE 13(2): e0192770 (2018).

(Continued)

*Primary Examiner* — Pranav N Patel

(57) ABSTRACT

The present invention provides a method for hemodiafiltration which applies dialysate gradient across a multi-chambered hemodiafiltrator having a plurality of compartmentalized tubular dialysate chambers. An acidic dialysate with urea at a concentration is applied to a first dialysate chamber. A less acidic dialysate with a lower concentration of urea than those for the first dialysate chamber is applied to a second dialysate chamber. A basic dialysate with no urea but with ammonia at a concentration up to a concentration detected in normal human blood is applied to a last dialysate chamber. The concentrations of urea for the first and second dialysate chambers decrease over time to zero prior to conclusion of hemodiafiltration.

13 Claims, 8 Drawing Sheets

(56) References Cited

U.S. PATENT DOCUMENTS

| | | |
|---|---|---|
| 6,719,907 B2 | 4/2004 | Collins et al. |
| 6,776,912 B2 | 8/2004 | Baurmeister |
| 6,821,441 B2 | 11/2004 | Pedrini et al. |
| 7,067,060 B2 | 6/2006 | Collins et al. |
| 7,074,332 B2 | 7/2006 | Summerton et al. |
| 7,285,106 B2 | 10/2007 | Collins et al. |
| 7,534,349 B2 | 5/2009 | Collins et al. |
| 9,610,393 B2 | 4/2017 | Rada et al. |
| 9,700,661 B2 | 7/2017 | Gerber et al. |
| 9,827,361 B2 | 11/2017 | Pudil et al. |
| 2002/0053540 A1 | 5/2002 | Collins et al. |
| 2006/0041216 A1 | 2/2006 | McLaughlin et al. |
| 2010/0096329 A1 | 4/2010 | Kotanko et al. |
| 2011/0120930 A1 | 5/2011 | Mishkin |
| 2012/0253022 A1 | 10/2012 | Kotanko et al. |
| 2014/0158588 A1 | 6/2014 | Pudil et al. |
| 2014/0197105 A1 | 7/2014 | DiBiasio et al. |
| 2015/0188162 A1 | 7/2015 | Lee et al. |
| 2015/0258268 A1 | 9/2015 | Collier et al. |
| 2015/0283315 A1 | 10/2015 | Cho |
| 2015/0306298 A1 | 10/2015 | Tschulena et al. |
| 2015/0343134 A1 | 12/2015 | Tschulena et al. |
| 2016/0074570 A1 | 3/2016 | Cho |
| 2017/0021075 A1 | 1/2017 | Doyle et al. |
| 2017/0216513 A1 | 8/2017 | Fabig |
| 2017/0340795 A1* | 11/2017 | Charest ............... A61M 1/3431 |
| 2018/0028739 A1 | 2/2018 | Mishkin et al. |
| 2018/0221554 A1 | 8/2018 | Mazack et al. |
| 2018/0369783 A1 | 12/2018 | Baier-Goschutz et al. |
| 2019/0054226 A1 | 2/2019 | Tumlin |

FOREIGN PATENT DOCUMENTS

| | | |
|---|---|---|
| WO | WO2001024849 A1 | 4/2001 |
| WO | WO2001047580 A1 | 7/2001 |

OTHER PUBLICATIONS

Weiner I.D, Verlander J.W: Ammonia transporters and their role in acid base balance Physiol Rev 97: 467-494, 2017.

Wingfield P.T: Protein precipitation using ammonia sulfate Curr Protoc Protein Sci May 2001; Appendix 3: Appendix 3F.

Eloot S, Schneditz D, Cornelis T, et al: Protein bound uremic toxin profiling as a tool for optimizing hemodialysis PLoS ONE 11(1): e0147159 (2018).

Auton M, Holthauzen LMF, Bolen D.W: Anatomy of energetic changes accompanying urea induced protein denaturation PNAS 2007; 104(39); 15317-15322.

* cited by examiner

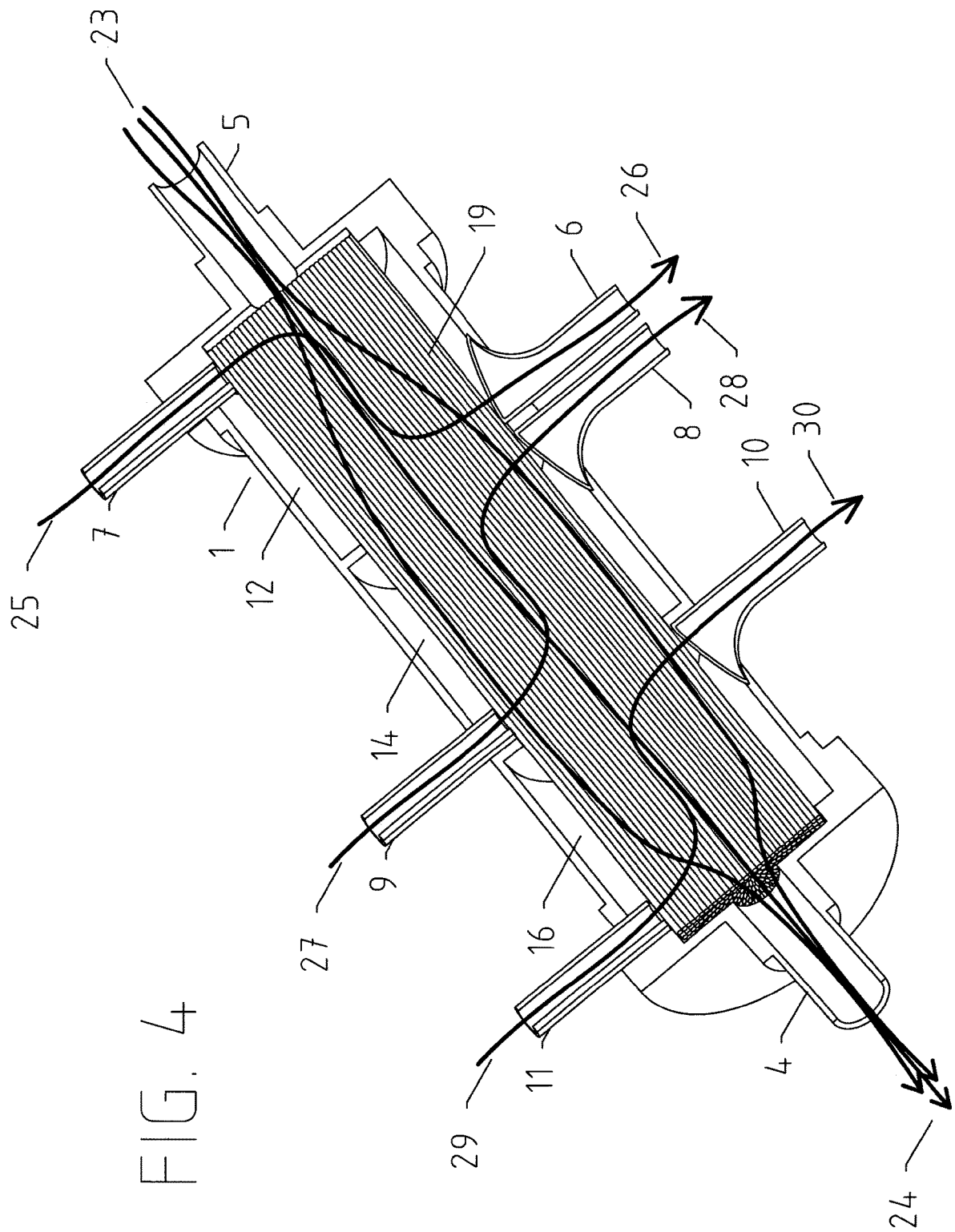

GRADIENT DIALYSATE HEMODIAFILTRATION

CROSS REFERENCE TO RELATED APPLICATIONS

Related applications are disclosed in the Information Disclosure Statement, in compliance with 37 CFR 1.78 and MPEP $211 et seq.

TECHNICAL FIELD

The present invention relates generally to the field of blood dialysis. More specifically, the present invention provides a method for clinical hemodiafiltration for patients in renal failure.

BACKGROUND OF THE INVENTION

Modern hemodialysis including hemodiafiltration has been advanced to a point that a majority of uremic toxins of small water-soluble molecules (<0.5 kD) and a number of toxins of middle molecules (0.5-60 kD) can be readily removed from blood of uremic patients. However, about a quarter of all the uremic toxins are known to be protein bound molecules, and so far there has not been a hemodialysis (including hemodiafiltration) device or a technology effectively eliminating these protein bound uremic toxins from the blood for clinical use. Recent discoveries and understanding of pathophysiological relationship between the protein bound uremic toxins and cardiovascular morbidity and mortality highlight an urgent need to develop a new technology that would allow efficient and therapeutically effective removal of the protein bound uremic toxins from the blood.

A number of studies revealed that the protein bound uremic toxins are removed by active secretory processes at proximal convoluted renal tubules. However, mechanisms of transporting the protein bound uremic toxins from the blood to a tissue side of the proximal convoluted tubular epithelial cells are not known and elusive. At least for our understanding of an early process of freeing the protein bound uremic toxins from binding proteins, a key process should be that electrostatic charges of protein residues binding the protein bound uremic toxins should change to a point that there come unfolding of a tertiary structure of the binding proteins, and neutralization of non-covalent and covalent binding forces of the protein residues. This critical first step, in fact, occurs in glomeruli through which the blood loses a major portion of bicarbonate by passive filtration averaging about 4200 mmol/day for adults with normal renal function, thereby significantly lowering a pH of the blood in efferent blood vessels coming out from glomerular vascular complexes until the bicarbonate, reabsorbed and newly made in proximal and distal convoluted tubules, respectively, is reclaimed back to the blood that is existing from a network of efferent peritubular capillaries. The peritubular capillaries are closely intertwined with the proximal and distal convoluted tubules in the cortical and medullary portions of the renal tissue. It stands to reason that the critical first step of unbinding of the protein bound uremic toxins from the binding proteins to become "freed protein bound uremic toxins" occurs in an acidified blood over a segment of the peritubular capillaries by the loss of the bicarbonate from the blood through the glomeruli since an average iso-electric point (pI) of blood proteins is known to around 6.8 including serum albumin.

Unless the protein bound uremic toxins are released free from the binding proteins and removable (dialysable; diafiltrarable), it would be difficult for currently available hemodialysis (including hemodiafiltration) devices and technologies to successfully remove the protein bound uremic toxins from the blood of the uremic patients. Based on the acidification of the blood in the efferent peritubular capillaries existing from the glomeruli following glomerular filtration described above, it can be accomplished first by acidifying the blood in a hemodialysis (including hemodiafiltration) system so as to free the protein bound uremic toxins from the binding proteins, secondly by removing the freed protein bound uremic toxins from the blood by the hemodialysis and the hemodiafiltration, and thirdly by normalizing a pH of the acidified blood before it returns to the patient. In laboratories over many decades, this particular method of separating protein bound molecules from the binding protein has been well known as "iso-electric focusing". Since dialysate is produced by a proportioning system combining bicarbonate as a base (alkaline) source with lactate, citric acid, or glacial acetic acid as an acid source, a range of dialysate solutions, with each dialysate solution having a different pH from other dialysate solutions, can be straightforwardly produced by programming the proportioning system so as to vary concentrations of each component in a final mixture of a particular dialysate solution.

The acidification of the blood from the human body drawn into a packed bundle of hollow fibers of hemodialyzer or hemodiafiltrator so as to lower the pH of the blood to a preset level such as 6.0 can be accomplished by a first dialysate solution having a higher concentration of the acid source than a usual proportioning concentration ratio of "1 of acid:1.72 of base:42.28 of water" for the current hemodialysis. Similarly, normalization of the pH of the acidified blood by the acidification in the hollow fibers back to 7.35-7.45 can be achieved by a second dialysate solution having a higher concentration of the base source than the usual proportioning concentration ratio. The second dialysate solution is configured to neutralize an excess H+ of the blood donated by the first dialysate solution, before the blood returns to the human body. It is advantageous to sequence the acidification of the blood and the neutralization of the pH of the acidified blood in tandem over a single unit of the packed bundle of the hollow fibers in order to reduce an overall shear stress imposed on blood cells going through the hollow fibers. Furthermore, it may be necessary to forcefully flush out the freed protein bound uremic toxins from the acidified blood by the hemodialysis or the hemodiafiltration since a majority of charged moieties of the freed protein bound uremic toxins may be altered for their electrostatic state in the acidifying dialysate to a point that water solubility of the freed protein bound uremic toxins may be adversely affected. One issue of the forceful removal of the freed protein bound uremic toxins by the hemodialysis and the hemodiafiltration would be that a significant portion of normal proteins of the acidified blood would be in an unfolded configuration, thereby vulnerable to a shear stress of the dialysate going through the normal proteins. It is yet unknown as to whether the shear stress by the dialysate to the normal proteins in the unfolded configuration would impact on a range of function of the normal proteins following the normalization of the pH of the acidified blood. This unique issue may be minimized by limiting a volume of the acidified blood to be exposed to the shear stress of the dialysate for the forceful removal of the freed protein bound uremic toxins. This can be accomplished by compartmentalizing and minimizing a portion of a hemodialyzer (including hemodiafiltrator) for the forceful removal of the freed protein bound uremic toxins, separating from a portion for the acidification of the blood and from a portion for the normalization of the pH of the acidified blood.

A second factor for consideration of binding and unbinding of protein bound uremic toxins to and from, respectively, blood proteins is presence of urea. A high concentration of urea is well known for its potential for denaturing nascent proteins (unfolding a tertiary structure of proteins) by hydrogen bonding mechanisms and non-hydrogen bonding mechanisms. Although there is no known level of blood urea as a threshold point for an unfolded configuration of the blood proteins, it stands to reason that patients with chronic renal failure having higher concentrations of blood urea than that of normal person have an increase in degree and concentration of the blood proteins in the unfolded configuration which favor release of the protein bound uremic toxins from binding sites of the blood proteins to a blood compartment in a form of freed protein bound uremic toxins. Hemodialysis and hemodiafiltration which are highly effective in removing small water soluble molecules including urea reduces the urea much more efficiently than removing middle molecules to which protein bound uremic toxins belong. Consequently, in an early phase of hemodialysis and hemodiafiltration, the blood urea is removed rapidly and concentration of the blood urea decreases substantially before the freed protein bound uremic toxins can be removed from the blood. Rapid reduction in the concentration of the blood urea by the hemodialysis and hemodiafiltration before removal of the freed protein bound uremic toxins from the blood promotes refolding of the blood proteins from the unfolded configuration. The blood proteins in the refolded configuration then bind the freed protein bound uremic toxins in the blood, resulting in no net changes in concentration of "bound fraction+freed fraction" of the protein bound uremic toxins. In between sessions of the hemodialysis and the hemodiafiltration, the concentration of the blood urea inevitably increases in the patients with the chronic renal failure, thereby promoting the unfolded configuration of the blood proteins, which then results in release of the protein bound uremic toxins from the binding sites of the blood proteins into the blood compartment of the freed protein bound uremic toxins. If an abnormally high concentration of the urea is maintained without change in a portion of a hemodialyzer and a hemodiafiltrator during the hemodialysis and the hemodiafiltration, respectively, the blood proteins in the unfolded configuration would not be able to bind back the freed protein bound uremic toxins which then can be removed by ongoing hemodialysis and the hemodiafiltration.

A third factor to consider for folding and unfolding of the tertiary structure of the proteins having binding sites for the protein bound uremic toxins is blood ammonia that is newly synthesized by and transported from medullary tissues of kidney to peritubular capillaries and renal veins. Although we lack a full understanding on physiologic and biochemical contribution of blood ammonia to homeostasis of renal function, ammonia has been well known for its vital contribution to production of bicarbonate in the medullary tissues of the kidney. Unlike breath ammonia level, blood ammonia level has been shown to be remarkably steady even in patients with fully blown chronic renal failure requiring dialysis, without much difference from that of normal people. High levels of blood ammonia are a well known detrimental factor for the human body, and the blood ammonia is known to be metabolized by liver so as to maintain the steady state of the blood ammonia level. In one study, an average blood ammonia level of the patients with chronic renal failure was approximately 20 micro-mol/L, whereas the level in normal individuals was 25 micro-mol/L without statistical differences. It is well known that about 50% of newly synthesized ammonia from the medullary tissues of the kidney is transported into the blood via the peritubular capillaries, and the other half is used to maintain acid-base homeostasis by generation of bicarbonate and as secretable ammonia in urine especially in a setting of metabolic acidosis. Furthermore, the blood level of ammonia was shown to increase upon the hemodialysis in the study from 21 micro-mol/L to 23 micro-mol/L. All of these indicate that there is a feedback loop system in the human body comprising the liver and kidneys tightly regulating the level of blood ammonia, and that there should be a physiologic role for transported ammonia across the peritubular capillaries from the medullary tissues to the blood since both transportation process of ammonia and metabolism of the transported ammonia by the liver require an input of energy. As of now, we do not have good understanding on the physiologic role of the transported ammonia, especially on the folding and unfolding of the tertiary structure of the blood proteins in the peritubular capillaries, except that ammonia has a molecular dipole moment of 1.47 D indicating presence of charged polarity. Water has the molecular dipole moment of 1.85 D, and is known to form a hydration layer on a surface of proteins and maintain solubility of the proteins.

In laboratory settings, presence of salts such as $(NH_4)_2SO_4$ above a concentration of 0.15 M~0.5M increases surface tension of the water molecules, promoting precipitation of the proteins due to increased hydrophobic interaction between the water molecules and the proteins (salting-out). Below the concentration of 0.15 M~0.5M, the tertiary structure of the proteins begins unfolding (salting-in), thereby increasing solubility of the proteins. According to Hofmeister series, $(NH_4)_3PO_4$ is more effective than $(NH_4)_2SO_4$ for solvation of the proteins, and is within a range of solutes affecting solubility of the proteins. It is yet to be investigated as to whether transported $NH_4^+$ in the peritubular capillaries from the medullary tissues is to be combined with free $PO_4^{3-}$ present in the blood in a form of $(NH_4)_3PO_4$, whether concentration of $(NH_4)_3PO_4$ in patients with an elevated concentration of $PO_4^{3-}$ in the blood due to chronic renal failure continues to be below 0.15M~0.5M, thereby favoring an unfolded configuration of the tertiary structure of the blood proteins, or whether the concentration of $(NH_4)_3PO_4$ in the patients with the elevated concentration of $PO_4^{3-}$ in the blood due to the chronic renal failure is above the threshold for the solubility of the protein, thereby promoting a folded configuration of the tertiary structure of the blood proteins. It also stands to reason that unfolded blood proteins in a proximal portion of the peritubular capillaries associated with a sudden lowering of pH of the blood due to the glomerular filtration of bicarbonate from the blood need to be refolded in a distal portion of the peritubular capillaries after having released the protein bound uremic toxins back to their nascent tertiary configuration for proper functioning before returning back to systemic circulation. This refolding process of the blood proteins can be accomplished by reabsorbing bicarbonate in the distal portion of the peritubular capillaries, thus normalizing pH of the blood. The refolding process can be assisted by ammonia per se transported into the distal portion of the peritubular capillaries from the medullary tissues, as ammonia ($NH_4^+$) is the most effective cation in the Hofmeister series on maintaining a folded configuration of the tertiary structure of proteins. It would be advantageous for the refolding process of the denatured (unfolded) proteins to add ammonia to a dialysate at a concentration similar to that found in the blood, near a distal end of a hemodialyzer and a hemodiafiltrator just prior to sending hemodialyzed/hemodiafiltrated blood back to the systemic circulation of a patient. The refolded blood proteins in the systemic circulation, with their binding sites being emptied by the hemodialysis or the hemodiafiltration, should then be able to bind free protein bound uremic toxins in the blood. Obviously patients with liver disorders or inherited disorder of ammonia metabolism cannot receive any additional ammonia during hemodialysis and hemodiafiltration as an increased level of ammonia in the systemic circulation may induce a serious harm to the patients.

In a clinical scenario of a patient in a metabolic acidosis and uremia due to a significant renal failure undergoing the hemodialysis or the hemodiafiltration, a following sequence of biochemical changes would occur: 1. Excess level of metabolic acids and an excess concentration of blood urea in vivo, promoting release of the protein bound uremic toxins from the binding proteins to become the freed protein bound uremic toxins in circulation and inside cells in vivo, thus inciting damages to exposed tissues and the cells; 2. Immediate correction of a pH of an acidified blood by the metabolic acidosis by the hemodialysis (including the hemodiafiltration) with a bicarbonate-rich dialysate and a rapid reduction of the concentration of the blood urea by said hemodialysis and hemodiafiltration, making the freed protein bound uremic toxins bound back to the binding sites of the proteins; 3. Return of a dialyzed/diafiltrated blood in a normal pH and a reduced blood urea having the protein bound uremic toxins fully bound to the binding sites of the binding protein to the patient; 4. Mixing of the dialyzed blood in the normal pH and the reduced blood urea with the acidified blood having the excess blood urea occurs in the systemic circulation, thereby lowering the pH of the dialyzed blood in vivo and increasing the concentration of the blood urea from the reduced level, thereby freeing the protein bound uremic toxins from the binding proteins and releasing them back to the patient; 5. Largely unchanging concentrations of the freed protein bound uremic toxins in the circulation and the cells in vivo; 6. Ongoing toxicity from the protein bound uremic toxins despite the hemodialysis and the hemodiafiltration.

Based on the aforementioned biochemical and physiologic understanding on changes in the concentration of the protein bound uremic toxins from a perspective of the folding and unfolding the tertiary structure of the blood proteins, I propose a method of hemodiafiltration using a compartmentalized hemodiafiltrator that allows sequential increases in pH of dialysates from about 6.0 (>5.5~<6.5) to about 8.0 (>7.5~<8.5) across iso-electric points of the blood proteins through a plurality of compartmentalized tubular dialysate chambers of the compartmentalized hemodiafiltrator; that allows sequential gradient transitions in urea concentration of the dialysate from a concentration equivalent to a patient's concentration of the blood urea at initiation of a session of the hemodiafiltration to no urea prior to conclusion of the session of the hemodiafiltration so as to maintain and gradually remove the urea from the patient's blood; that allows addition of ammonia in solution in the dialysate up to a blood level of ammonia expected in a normal individual (20~25 micro-mol/L) immediately prior to sending the dialyzed blood back to the systemic circulation of the patient. A first dialysate having an acidic pH with a concentration of urea runs through a first dialysate chamber and is drained out through a first dialysate output tube. The first dialysate is configured to have a gradual decrease in the urea concentration over time from an initial concentration equivalent to or slightly less than a concentration of the blood urea in the patient at the initiation of a session of hemodiafiltration to a zero concentration prior to the conclusion of the session of the hemodiafiltration. A second dialysate which comprises a less acidic pH dialysate, and a lower concentration of the urea than those of the first dialysate runs through a second dialysate chamber and is drained out through a second dialysate output tube. A last dialysate runs through a last dialysate chamber and is drained out through a last dialysate output tube, wherein the last dialysate comprises a basic pH dialysate, no urea and a concentration of ammonia in solution up to a normal level of ammonia found in normal individuals (20~25 micro-mol/L).

SUMMARY OF THE INVENTION

In one embodiment, the present invention of hemodiafiltration utilizes a plurality of dialysates for a single session of the hemodiafiltration by a multi-chambered hemodiafiltrator in order to enhance removal of protein bound uremic toxins from blood of a patient in renal failure. Each dialysate is different in pH, urea concentration and ammonia concentration from each other dialysate. The present invention comprises the multi-chambered hemodiafiltrator which is connected to at least a first set of a first dialysate vessel with a first urea vessel, to a second set of a second dialysate vessel with a second urea vessel, and to a last set of a last dialysate vessel with a last ammonia vessel. The multi-chambered hemodiafiltrator comprises a single tubular cylinder which is compartmentalized into a proximal blood chamber, a dialysate tubular cylinder, and a distal blood chamber. A packed bundle of hollow fibers for blood flow is enclosed coaxially along a longitudinal axis inside the dialysate tubular cylinder. The dialysate tubular cylinder is disposed in the middle of the hemodiafiltrator, adjoining proximally the proximal blood chamber and distally the distal blood chamber. The dialysate tubular cylinder is compartmentalized by at least two inner circumferential dividers protruding from an inner circumferential wall of the dialysate tubular cylinder into three compartmentalized tubular dialysate chambers arranged in tandem along the longitudinal axis of the hemodiafiltrator.

In one embodiment, a first dialysate chamber adjoins proximally the proximal blood chamber, and a third dialysate chamber adjoins distally the distal blood chamber. A second dialysate chamber adjoins proximally the first dialysate chamber and distally the third dialysate chamber. A dialysate flow in the first dialysate chamber is concurrent with a blood flow inside the packed bundle of the hollow fibers. A dialysate flow in the second and another dialysate flow in the third dialysate chambers are countercurrent to the blood flow inside the packed bundle of the hollow fibers. The proximal blood chamber leakproofly encircles a proximal portion of a packed bundle of hollow fibers, and the distal blood chamber leakproofly encircles a distal portion of the packed bundle of the hollow fibers. The proximal blood chamber is coaxially aligned with the distal blood chamber, and both the proximal and distal blood chambers are coaxially aligned with the packed bundle of the hollow fibers. A blood intake tube coaxially adjoins the proximal blood chamber and a blood output tube coaxially adjoins the distal blood chamber, so as to establish a coaxially linear path of the blood flow from the blood intake tube through the packed bundle of the hollow fibers to the blood output tube.

In one embodiment, the dialysate tubular cylinder coaxially encloses the packed bundle of the hollow fibers. A compartmentalized configuration of the tandem arrangement of the compartmentalized tubular dialysate chambers comprises the first dialysate chamber for hemodiafiltration with acidification of blood going through a proximal portion of the packed bundle of the hollow fibers by a first dialysate having a low concentration of bicarbonate so as to maintain a pH at around 6.0 and a urea at a concentration over a range from an initial concentration at start of a session of hemodiafiltration equivalent to or slightly less than a concentration of the blood urea in the patient transitioning to a zero concentration over time at conclusion of the session of the hemodiafiltration; a second dialysate chamber for hemodiafiltration of a mid portion of the packed bundle of the hollow fibers with a second dialysate having a higher concentration of bicarbonate and a lower concentration of the urea than those of the first dialysate; the third dialysate chamber for hemodiafiltration and normalization of a pH (7.35~7.45) of the blood in a distal portion of the packed bundle of the hollow fibers by a third dialysate having a higher concentration of bicarbonate so as to maintain a pH up to 8.0 than the dialysates for the first and second dialysate chambers. The third dialysate contains no urea but ammonia in solution at a concentration of up to 20~25 micro-mol/L. Each compartmentalized tubular dialysate chamber coaxially adjoins along a longitudinal axis and is compartmentalized from each other compartmentalized tubular dialysate chamber by the inner circumferential divider protruding from the inner circumferential wall of the dialysate tubular cylinder. Each compartmentalized tubular dialysate chamber comprises a dialysate intake tube and a dialysate output tube, and each dialysate intake tube is configured to supply a unique dialysate dedicated for each compartmentalized tubular dialysate chamber.

In one embodiment, a diameter of an inner rim of the inner circumferential divider is shorter than a diameter of the inner circumferential wall of the compartmentalized tubular dialysate chambers by at least 1 mm so as to provide an outer circumferential space of a measurable dimension between an outer peripheral layer of the packed bundle of the hollow fibers and the inner circumferential wall of the tubular chambers. The inner circumferential divider is provided in a rectangular bar configuration on a longitudinal cross section. A diameter of the inner circumferential divider is nearly equivalent to a diameter of the packed bundle of the hollow fibers, so as to tightly encircle a portion of the outer peripheral layer of the packed bundle of the hollow fibers. The outer circumferential space serves as compartmentalized reservoir to retain the dialysate which runs through the outer circumferential space of each compartmentalized tubular dialysate chamber from the dialysate intake tube to the dialysate output tube.

In one embodiment, the first dialysate in the first dialysate chamber is admixed with the second dialysate in the second dialysate chamber across a boundary (transitional) region of the packed bundle of the hollow fibers encircled by the first inner circumferential divider by a process of passive to and fro diffusion between the first and second dialysates flowing in between individual hollow fibers of the packed bundle of the hollow fibers. The packed bundle of the hollow fibers is tightly encircled by the inner circumferential dividers about the outer peripheral layer of the packed bundle of the hollow fibers. The boundary region of the packed bundle of the hollow fibers is configured as a transverse cross-sectional columnar region of the packed bundle of the hollow fibers tightly encircled by the inner circumferential divider partitioning a portion of the packed bundle of the hollow fibers into two half portions of the packed bundle of the hollow fibers. A proximal half portion of the packed bundle of the hollow fibers disposed proximal to the transverse cross-sectional columnar region is encased in the first dialysate chamber and a distal half portion of the packed bundle of the hollow fibers disposed distal to the transverse cross-sectional columnar region is encased in the second dialysate chamber. The proximal half portion of the packed bundle of the hollow fibers continues to become the distal half portion of the packed bundle of the hollow fibers across the transverse cross-sectional region. The boundary region of the packed bundle of the hollow fibers is a three-dimensional columnar volume and coaxially aligned with a longitudinal axis of the packed bundle of the hollow fibers.

In one embodiment, a width (longitudinal length) of the inner circumferential divider measured along a longitudinal axis of the compartmentalized tubular dialysate chambers is made as a determining factor for letting the first dialysate in the first dialysate chamber admixed with the second dialysate in the second dialysate chamber across the boundary region of the packed bundle of the hollow fibers. A wider columnar volume of mixing between the first and second dialysates over a wider columnar dimension of the boundary region would occur with an inner circumferential divider having a wider width, compared to a columnar volume of the mixing with an inner circumferential divider having a narrower width resulting in a narrower columnar dimension of the boundary region of the packed bundle of the hollow fibers. The mixing of the first and second dialysates by the passive to and fro diffusion at the boundary region of the packed bundle of the hollow fibers serves to produce a continuous gradient of the pH and the urea concentration in a dialysate mixture produced by the mixing of the first and second dialysates. The inner circumferential divider having the wider width would produce a less steep gradient in the dialysate mixture over the wider columnar dimension at the boundary region, compared to the inner circumferential divider having the narrower width which would result in a steeper gradient over the narrower columnar dimension at the boundary region. The wider inner circumferential divider producing a less steep pH gradient in the dialysate mixture at the boundary region would be better suited for removal of protein bound uremic toxins from proteins having a wider range of iso-electric points. The narrower inner circumferential divider producing the steeper pH gradient in the dialysate mixture would be better suited for removal of protein bound uremic toxins from proteins having a narrower range of iso-electric points. An inner circumferential divider compartmentalizing the third dialysate chamber from the second dialysate chamber is similarly configured to the aforementioned configuration of the inner circumferential divider compartmentalizing the first dialysate chamber from the second dialysate chamber.

In one embodiment, the protein bound uremic toxins are removed from the blood in the packed bundle of the hollow fibers in the first and second dialysate chambers and around the boundary regions established by the inner circumferential dividers by the dialysates having low concentrations of bicarbonate in the dialysate proportioning concentration ratio. A pH of the dialysate in the first dialysate chamber would range from 5.5 to 7.0, so as to acidify the blood in a proximal portion of the packed bundle of the hollow fibers housed in the first dialysate chamber. A pH of the dialysate in the second dialysate chamber would range from 6.0 to 7.0, so as to acidify the blood in a mid portion of the packed bundle of the hollow fibers housed in the second dialysate chamber. A blood pH in the boundary region of the packed bundle of the hollow fibers between the first and second dialysate chambers therefore is maintained in a non-discontinuous pH gradient increasing from 5.5 to 7.0. A pH of the third dialysate in the third dialysate chamber would range from 7.5 to 9.5 with a high concentration of bicarbonate in the dialysate proportioning concentration ratio, so as to normalize a pH of an outgoing blood back to a pH of 7.35-7.45 in a distal portion of the packed bundle of the hollow fibers existing the third dialysate chamber to the blood output tube. A blood pH in the boundary region of the packed bundle of the hollow fibers between the second and third dialysate chambers therefore is maintained in a non-discontinuous pH gradient increasing from 6.0 to 9.5. In this configuration, the protein bound uremic toxins having iso-electric points ranging from 5.5 to 9.5 of pH would be removed by iso-electric gradient with a successive and continuous stepping-up in the pH of the blood from the proximal portion of the packed bundle of the hollow fibers to the distal portion of the packed bundle of the hollow fibers.

In one embodiment, the first dialysate is to be combined with the urea that is separately added to the first dialysate so as to vary the concentration of the urea in the first dialysate over time during the session of the hemodiafiltration. The initial concentration of the urea at the start of the session of the hemodiafiltration would range from <20 mg/dL to >100 mg/dL, equivalent to or slightly less than a concentration of the blood urea in the patient, which then decreases over time of a session of hemodiafiltration to a zero concentration at conclusion of the session of the hemodiafiltration. The urea concentration of the second dialysate is 25% to 50% of the urea concentration in the first dialysate. Therefore, the boundary region of the packed bundle of the hollow fibers between the first and second dialysate chambers establishes a non-discontinuous cascading-down gradient in the urea concentration from the first dialysate to the second dialysate. As the third dialysate does not contain the urea, a second non-discontinuous cascading-down gradient in the urea concentration through the boundary region of the packed bundle of the hollow fibers between the second and third dialysate chambers is established.

In one embodiment, a concentration of the ammonia in solution of the third dialysate is up to about 20 micro-mol/L~25 micro-mol/L. Since the second dialysate does not contain the ammonia, an ammonia concentration gradient in the boundary region of the packed bundle of the hollow fibers between the second and third dialysate chambers ranges from zero micro-mol/L to 25 micro-mol/L. The boundary region of the packed bundle of the hollow fibers between the second and third dialysate chambers serves to introduces the ammonia in solution from the dialysates to the blood in the packed bundle of the hollow fibers in a linear upward gradient configuration.

In one embodiment, the urea at a concentration is provided in the first urea vessel, separate from the first dialysate that is stored in the first dialysate vessel. The urea in the first urea vessel is configured to be under a separate control for infusion from a control for infusion for the first dialysate from the first dialysate vessel. The urea in the first urea vessel is configured to be added to the first dialysate before the first dialysate enters the first compartmentalized tubular dialysate chamber. Similarly, the urea at a lower concentration than the urea for the first dialysate is provided in the second urea vessel, separate from the second dialysate that is stored in the second dialysate vessel. The urea in the second urea vessel is configured to be under a separate control for infusion from a control for infusion for the second dialysate from the second dialysate vessel. The urea in the second urea vessel is configured to be added to the second dialysate before the second dialysate enters the second compartmentalized tubular dialysate chamber. The ammonia in solution is provided in the last ammonia vessel, separate from the last dialysate that is stored in the last dialysate vessel. The ammonia in solution in the last ammonia vessel is configured to be under a separate control for infusion from a control for infusion for the last dialysate from the last dialysate vessel. The ammonia in solution in the last ammonia vessel is configured to be added to the last dialysate before the last dialysate enters the last compartmentalized tubular dialysate chamber.

In one embodiment, all of the controls for the infusion of the dialysates, the urea and the ammonia in solution are centrally coordinated by an electronic command control module. An outgoing blood from the distal blood chamber to the patient is monitored for pH, electrolytes such as potassium and bicarbonate, urea concentration and ammonia concentration at a regular interval during the session of the hemodiafiltration. Data of values of the pH, the electrolytes, the urea concentration and the ammonia concentration are fed in a feedback loop into the electronic command control module which then electronically modulates volume and speed of the infusion of each dialysate, the urea and the ammonia in solution to each relevant chamber of the multi-chambered hemodiafiltrator. Purpose of the electronic command control module is to assure of maintenance of safe and normalized range of the pH, the electrolytes, the urea concentration and the ammonia concentration of the outgoing blood from the distal blood chamber of the multi-chambered hemodiafiltrator to the patient.

BRIEF DESCRIPTION OF THE DRAWINGS

FIG. 4 depicts a schematic illustration of a flow pattern of dialysate and blood across the multi-chambered hemodiafiltrator.

DETAILED DESCRIPTION OF THE DRAWINGS

As described below, the present invention provides a method of hemodiafiltration for patients in renal failure whom require hemodiafiltration/hemodialysis for survival and health maintenance. The present invention utilizes a plurality of dialysates for a single session of the hemodiafiltration by a multi-chambered hemodiafiltrator. Each dialysate is different in pH, urea concentration and ammonia concentration from each other dialysate. The present invention comprises the multi-chambered hemodiafiltrator which is connected to at least a first set of a first dialysate vessel with a first urea vessel, to a second set of a second dialysate vessel with a second urea vessel, and to a last set of a last dialysate vessel with a last ammonia vessel. Control of infusion of each dialysate, urea and ammonia in solution to the multi-chambered hemodiafiltrator is centrally coordinated by an electronic central command module. It is to be understood that the descriptions are solely for the purposes of illustrating the present invention, and should not be understood in any way as restrictive or limited. Embodiments of the present invention are preferably depicted with reference to FIGS. 1 to 8, however, such reference is not intended to limit the present invention in any manner. The drawings do not represent actual dimension of devices, but illustrate the principles of the present invention.

Figure 1:
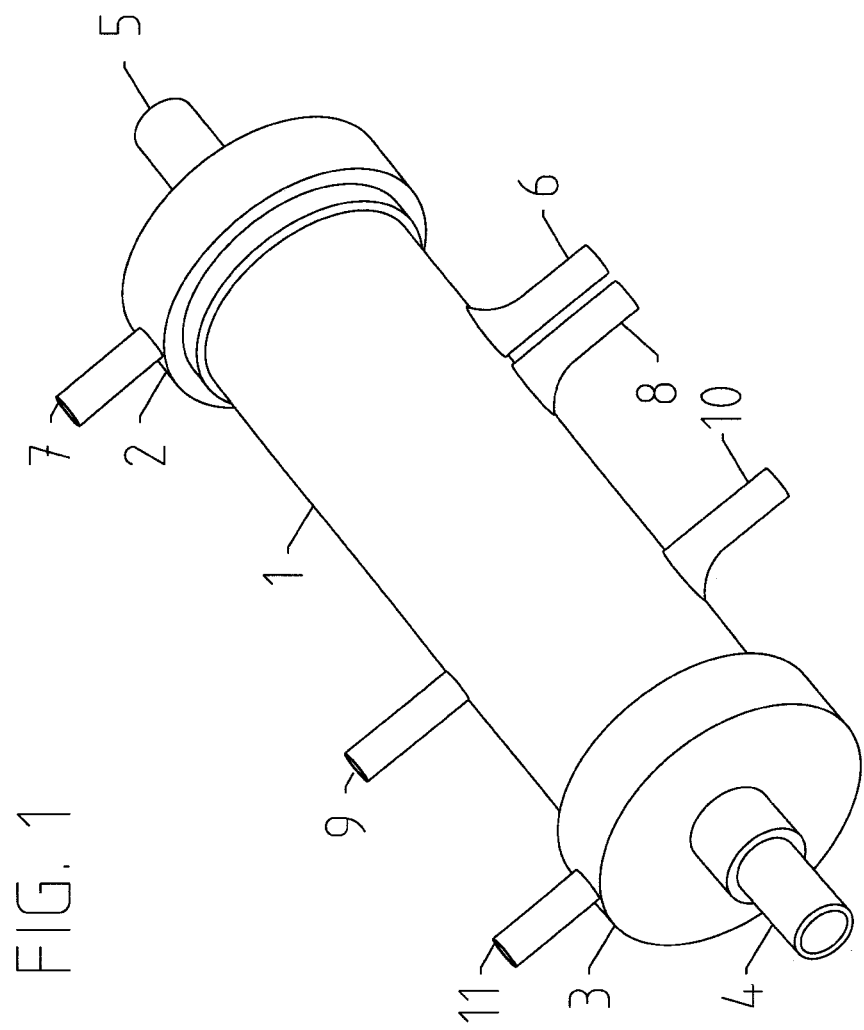
FIG. 1 shows a schematic three-dimensional view of a multi-chambered hemodiafiltrator.

A multi-chambered hemodiafiltrator shown in FIG. 1, provided in a cylindrical configuration, comprises the dialysate tubular cylinder 1, the proximal blood chamber 2 and the distal blood chamber 3. The proximal blood chamber 2 opens to and coaxially adjoins a blood intake tube 5, and the distal blood chamber 3 opens to and coaxially adjoins a blood output tube 4. The blood intake tube 5 and the blood output tube 4 are coaxially aligned along a longitudinal axis of the multi-chambered hemodiafiltrator. A first dialysate intake tube 7 perpendicularly adjoins and opens to a proximal portion of the dialysate tubular cylinder 1, and is configured to transmit a first dialysate across the proximal portion of the dialysate tubular cylinder 1 to a first dialysate output tube 6 perpendicularly connected and open to the proximal portion of the dialysate tubular cylinder 1. A second dialysate intake tube 9 perpendicularly adjoins and opens to a mid portion of the dialysate tubular cylinder 1, and is configured to transmit a second dialysate across the mid portion of the dialysate tubular cylinder 1 to a second dialysate output tube 8. A third dialysate intake tube 11 perpendicularly adjoins and opens to a distal portion of the dialysate tubular cylinder 1, and is configured to transmit a third dialysate across the distal portion of the dialysate tubular cylinder 1 to a third dialysate output tube 10. Blood flows from the blood intake tube 5 to the blood output tube 4 across the dialysate tubular cylinder 1. Therefore, the first dialysate flow from the first dialysate intake tube 7 to the first dialysate output tube 6 is concurrent with the blood flow; the second dialysate flow from the second dialysate intake tube 9 to the second dialysate output tube 8 is counter-current with the blood flow; the third dialysate flow from the third dialysate intake tube 11 to the third dialysate output tube 10 is counter-current with the blood flow.

Figure 2:
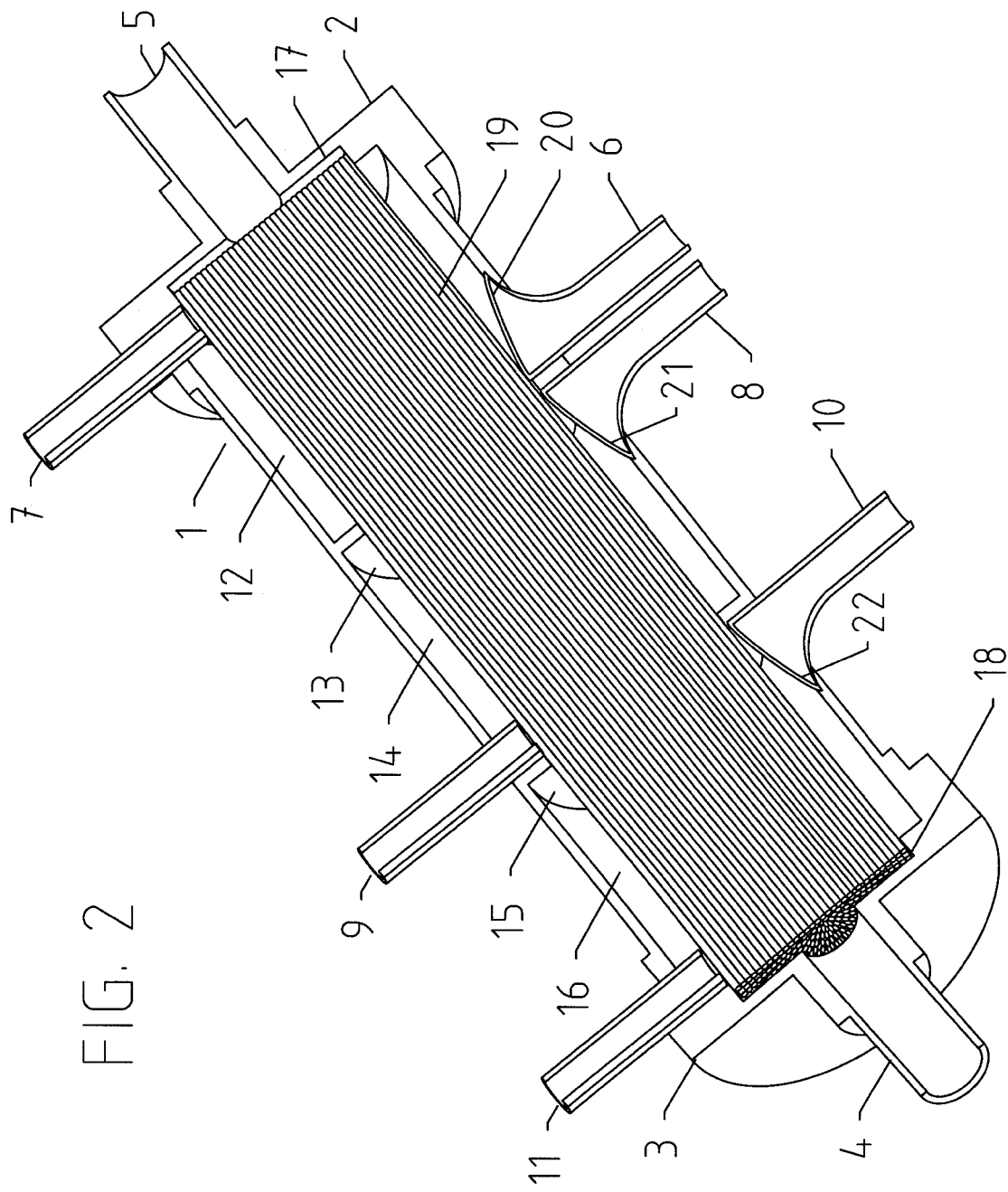
FIG. 2 represents a schematic three-dimensional exposed cut-out view of the multi-chambered hemodiafiltrator in an assembled configuration.

FIG. 2 represents a schematic three-dimensional exposed cut-out view of the multi-chambered hemodiafiltrator in an assembled configuration. The multi-chambered hemodiafiltrator, provided in a cylindrical configuration, comprises a proximal blood compartment 17 and a distal blood compartment 18. The blood intake tube 5 distally adjoins and opens to the proximal blood compartment 17, and the blood output tube 4 proximally adjoins and opens to the distal blood compartment 18. A proximal portion of the packed bundle of the hollow fibers 19 is leakproofly encased in the proximal blood compartment 17. A distal portion of the packed bundle of the hollow fibers 19 is leakproofly encased in the distal blood compartment 18. The dialysate tubular cylinder 1 comprises a first dialysate chamber 12, a second dialysate chamber 14 proximally adjoining the first dialysate chamber 12 and a third dialysate chamber 16 proximally adjoining the second dialysate chamber 14. The first dialysate chamber 12 proximally adjoins the proximal blood compartment 17. The first dialysate chamber 12 is separated from the second dialysate chamber 14 by a first inner circumferential divider 13 circumferentially protruding from an inner circumferential wall of the dialysate tubular cylinder 1. Similarly, the second dialysate chamber 14 is separated from the third dialysate chamber 16 by a second inner circumferential divider 15 circumferentially protruding from the inner circumferential wall of the dialysate tubular cylinder 1. A packed bundle of hollow fibers 19 in a cylindrical configuration on a radial cross-section is coaxially disposed inside the dialysate tubular cylinder 1.

Shown in FIG. 2, a circumferential space is provided between an outer peripheral layer of the packed bundle of the hollow fibers 19 and the inner circumferential wall of each compartmentalized tubular dialysate chamber 12, 14 and 16. The circumferential space is configured to serve as reservoir of the dialysate. A dimension of the circumferential space is determined by a radial length (height) of the inner circumferential dividers 13 and 15. The radial length is not less than 0.5 mm so as to provide the circumferential space a measurable dimension between the outer peripheral layer of the packed bundle of the hollow fibers 19 and the inner surface of the compartmentalized tubular dialysate chambers. An innermost part of the inner circumferential dividers 13 and 15 is configured to come into tight contact with the outer peripheral layer of the packed bundle of the hollow fibers 19, in order to separate each circumferential space of the compartmentalized tubular dialysate chamber from each other. In this configuration, a dialysate in each circumferential space does not get mixed with the other dialysate in the other circumferential space, except that the dialysates can diffuse through interfibrillar space in between individual hollow fibers of the packed bundle of the hollow fibers. The dialysate intake tubes 7, 9 and 11 are configured to abut at a right angle the outer peripheral layer of the packed bundle of the hollow fibers 19. Whereas the dialysate output tubes 6, 8 and 10 are open to the circumferential space of each compartmentalized tubular dialysate chamber. An opening of each dialysate output tube to the circumferential space is provided at a diagonal angle to the longitudinal axis of the dialysate tubular cylinder, in order to maximize an opening area of the dialysate output tube at a junction between the dialysate output tube and the circumferential space: a first opening area 20 of the first dialysate output tube 6; a second opening area 21 of the second dialysate output tube 8; a third opening area 22 of the third dialysate output tube 10.

Figure 3A:
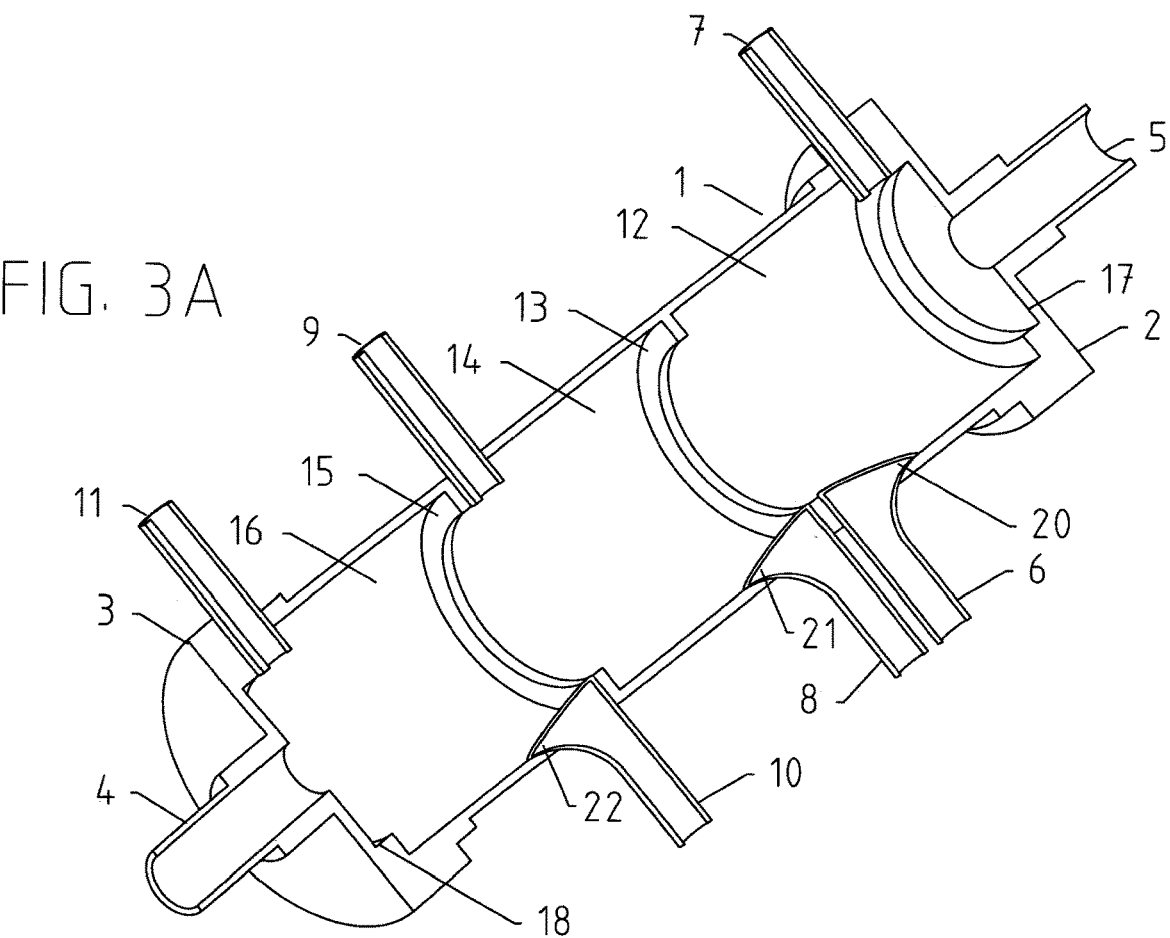
FIG. 3 illustrates a schematic three-dimensional exposed cut-out view of an outer casing and a packed bundle of hollow fibers.
Figure 3B:
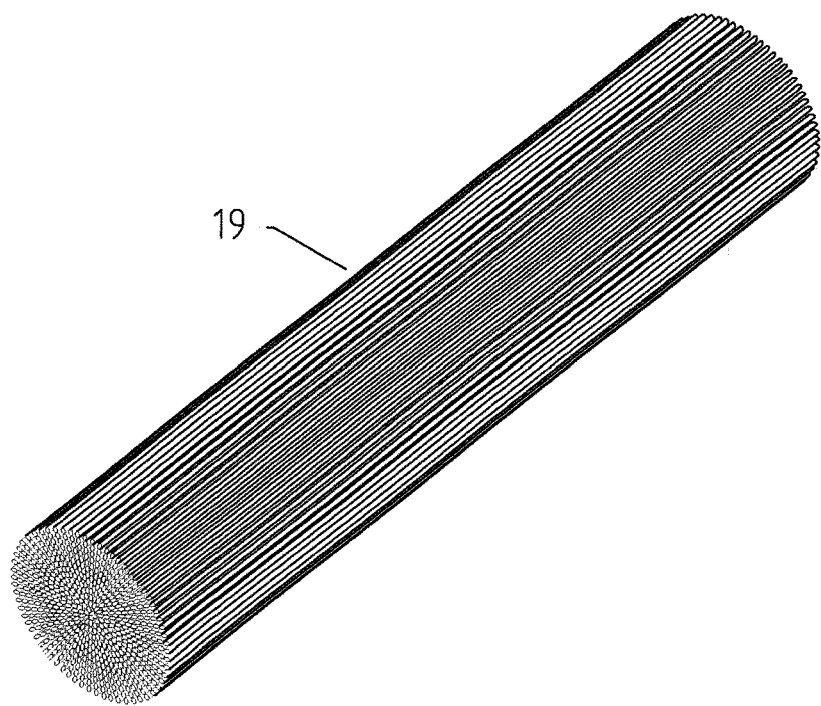
Figure 5A:
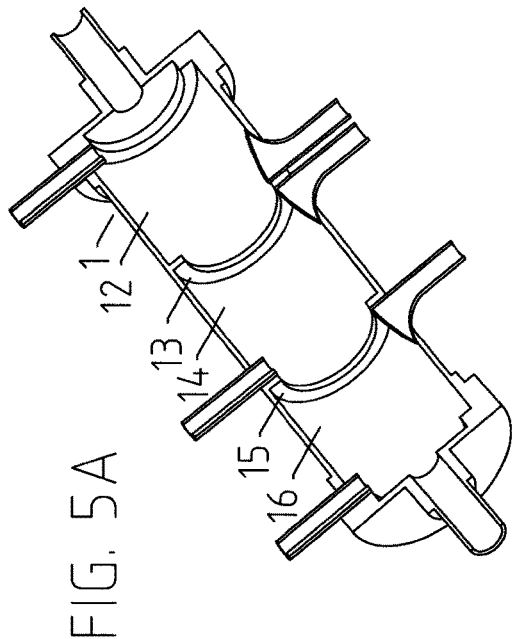
FIG. 5 show a schematic illustration of boundary regions of the packed bundle of the hollow fibers.
Figure 5B:
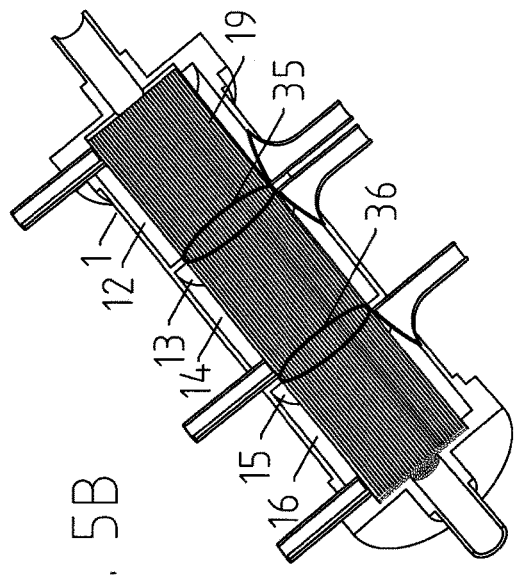
Figure 5C:
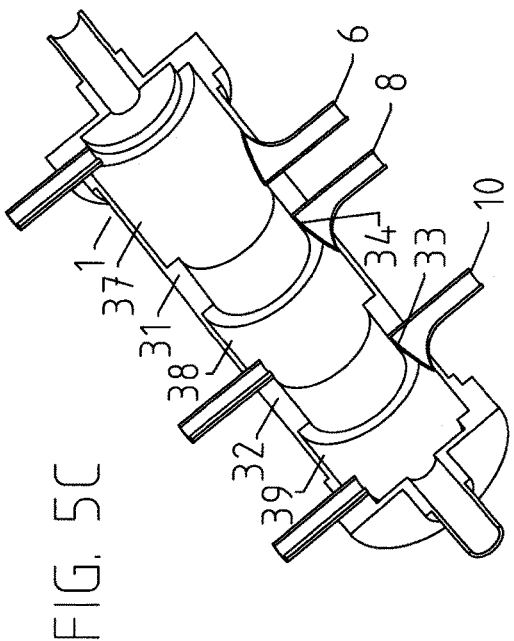
Figure 5D:
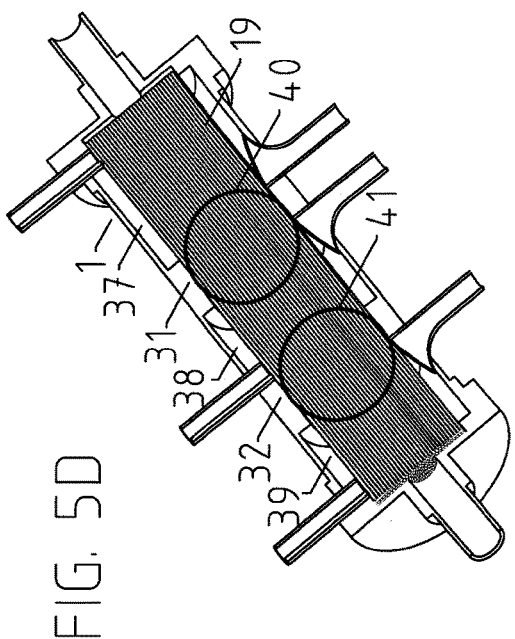

FIG. 3A illustrates a schematic three-dimensional exposed cut-out view of an outer casing of the multi-chambered hemodiafiltrator. The blood intake tube 5 coaxially adjoins and opens to the proximal blood compartment 17 of the proximal blood chamber 2. The blood output tube 4 coaxially adjoins and opens to the distal blood compartment 18 of the distal blood chamber 3. The blood intake tube 5 is coaxially aligned with the blood output tube 4 so as to direct blood flow longitudinally across the multi-chambered hemodiafiltrator. The dialysate tubular cylinder 1 is divided into three compartmentalized tubular dialysate chambers 12, 14 and 16 by the inner circumferential dividers 13 and 15, respectively. The dialysate intake tubes 7, 9 and 11 adjoin at the right angle and open to the dialysate tubular cylinder 1. The dialysate output tubes 6, 8 and 10 adjoin at the right angle but open at the diagonal angle to the dialysate tubular cylinder 1. The first dialysate intake tube 7 is disposed immediately adjacent to a distal side of a proximal portion of the dialysate tubular cylinder 1, and the first dialysate output tube 6 disposed immediately adjacent to a proximal side of the second inner circumferential divider 15, in order to generate a concurrent dialysate flow with the blood flow across the multi-chambered hemodiafiltrator. The second dialysate intake tube 9 is disposed immediately adjacent to a proximal side of the second inner circumferential divider 15, and the second dialysate output tube 8 disposed immediately adjacent to a distal side of the first inner circumferential divider 13, so as to generate a counter-current dialysate flow to the blood flow. Similarly, the third dialysate intake tube 11 is disposed immediately adjacent to a proximal side of a distal portion of the dialysate tubular cylinder 1, and the third dialysate output tube 10 disposed immediately adjacent to a distal side of the second inner circumferential divider 15. FIG. 3B shows a schematic example of the packed bundle of the hollow fibers in a typical cylindrical configuration.

FIG. 4 illustrates flow patterns of the dialysate and the blood across the multi-chambered hemodiafiltrator. An incoming blood 23 is taken in through the blood intake tube 5, coaxially goes through the packed bundle of the hollow fibers 19, and emerges from the blood output tube 4 as an outgoing blood 24. A first dialysate 25 is brought into the first dialysate chamber 12 through the first dialysate intake tube 7, tangentially runs through the packed bundle of the hollow fibers 19 and comes out from the first dialysate output tube 6 as an outgoing first dialysate 26, which is concurrent with the blood flow. The first dialysate flow is configured to be concurrent with the blood flow in order to maximize effects on release of protein bound uremic toxins from blood protein by inducing unfolding of binding sites of the blood proteins. A second dialysate 27 is delivered to the second dialysate chamber 14 through the second dialysate intake tube 9, tangentially flows through the packed bundle of the hollow fibers 19 and emerges out from the second dialysate output tube 8 as an outgoing second dialysate 28, which is countercurrent with the blood flow. A third dialysate 29 is brought in to the third dialysate chamber 16 through the third dialysate intake tube 11, tangentially runs through the packed bundle of the hollow fibers 19 and comes out from the third dialysate output tube 10 as an outgoing third dialysate 30, which is concurrent with the blood flow. The counter current flow of the second and third dialysates is configured to maximize removal of the released protein bound uremic toxins from the blood proteins by hemodiafiltration.

FIG. 5 show a schematic illustration of dimensional differences in boundary regions of the packed bundle of the hollow fibers by different widths of the inner circumferential divider measured along the longitudinal axis of the compartmentalized tubular dialysate chambers. FIGS. 5A-5B depict a narrow width of the first and second inner circumferential dividers 13 and 15, resulting in smaller columnar boundary regions 35 and 36 in the packed bundle of the hollow fibers 19, respectively. FIGS. 5C-5D illustrate a wider width of a first inner circumferential divider 31 and a second inner circumferential divider 32, resulting in bigger columnar boundary regions 40 and 41 in the packed bundle of the hollow fibers 19, respectively. Shown in FIG. 5C, a part of openings 34 and 33 of the second and third dialysate output tubes 8 and 9, respectively, into corresponding compartmentalized tubular dialysate chambers 38 and 39 is configured to open to the compartmentalized tubular dialysate chambers through a part of each inner circumferential divider 31 and 32. The first dialysate output tube 6 is not configured to open to a first dialysate chamber 37 through the first inner circumferential divider 31, in order to drain the first dialysate without resistance from a tightly abutted configuration of the packed bundle of the hollow fibers 19 to the first inner circumferential divider 31.

Figure 6B:
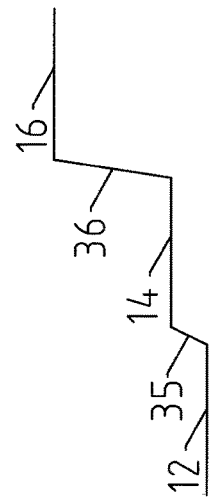
FIG. 6 shows a schematic illustration of a successive and continuous gradient of pH of the dialysates across the packed bundle of the hollow fibers of the multi-chambered hemodiafiltrator.
Figure 6D:
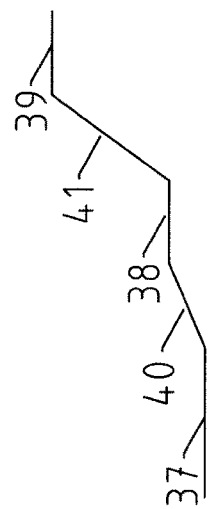
Figure 6A:
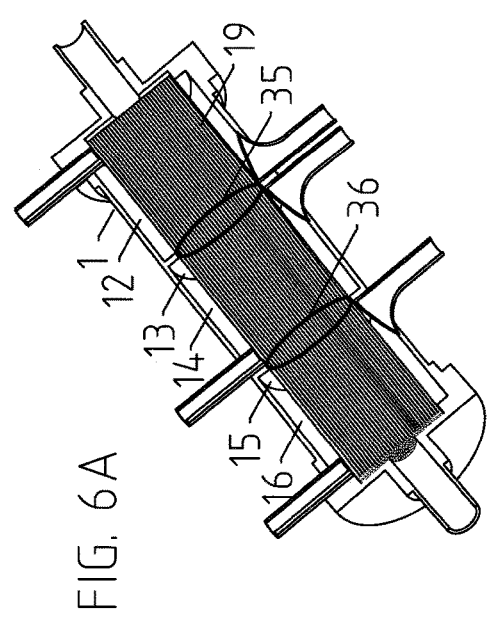

FIGS. 6A-6B show a schematic illustration of a successive and continuous gradient of pH of the dialysates across the packed bundle of the hollow fibers 19 of the multi-chambered hemodiafiltrator. A first dialysate in the first dialysate chamber 12 has a pH of 6.0, a second dialysate in the second dialysate chamber 14 has a pH of 6.4 and a third dialysate in the third dialysate chamber has a pH of 7.5 for this particular example. The width of the first and second inner circumferential dividers 13 and 15 is narrow, producing smaller volumes of the boundary regions 35 and 36, respectively. It shows a steep upward slope of transition in pH of a dialysate in the first boundary region 35 from the pH of the first dialysate in the first dialysate chamber 12 to the pH of the second dialysate in the second dialysate chamber 14. Similarly, a second upward slope of the transition in pH of a dialysate in the second boundary region 36 is steep, transitioning from the second dialysate in the second dialysate chamber 14 to the third dialysate in the third dialysate chamber 16.

Figure 6C:
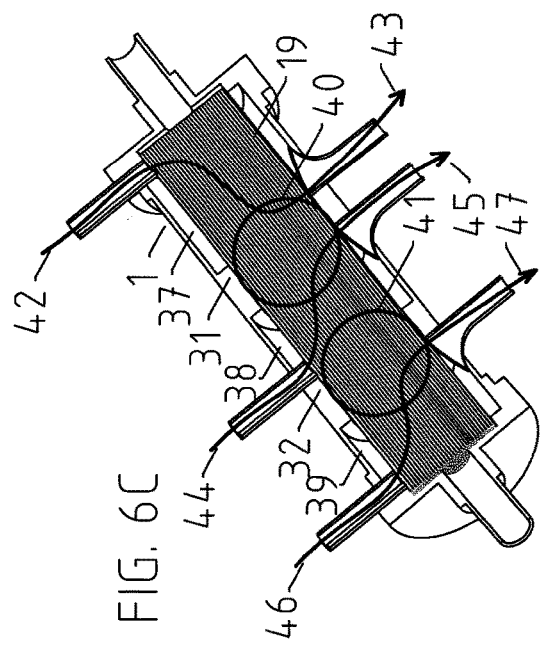

FIGS. 6C-6D show a schematic illustration of a less steep upward gradient of pH of the dialysates across bigger boundary regions 40 and 41 in the packed bundle of the hollow fibers 19, established by the wider inner circumferential dividers 31 and 32. It shows a less steep and more gradual upward slope of transition in pH of a dialysate in the first boundary region 40 from the pH of a first dialysate 42 in the first dialysate chamber 37 to the pH of a second dialysate 44 in the second dialysate chamber 38. Similarly, a second upward slope of the transition in pH of the second dialysate 44 in the second boundary region 39 is less steep and more gradual, transitioning from the second dialysate 44 in the second dialysate chamber 38 to a third dialysate 46 in the third dialysate chamber 39. The first dialysate 42 comes out as a first outgoing dialysate 43 after tangentially passing through the first boundary region 40 of the packed bundle of the hollow fibers 19 residing in the first dialysate chamber 37. The second dialysate 44 comes out as a second outgoing dialysate 45 after tangentially passing through the first boundary region 40 of the packed bundle of the hollow fibers 19 residing in the second dialysate chamber 38. The third dialysate 46 comes out as a third outgoing dialysate 47 after tangentially passing through the second boundary region 41 of the packed bundle of the hollow fibers 19 residing in the third dialysate chamber 39.

Figure 7A:
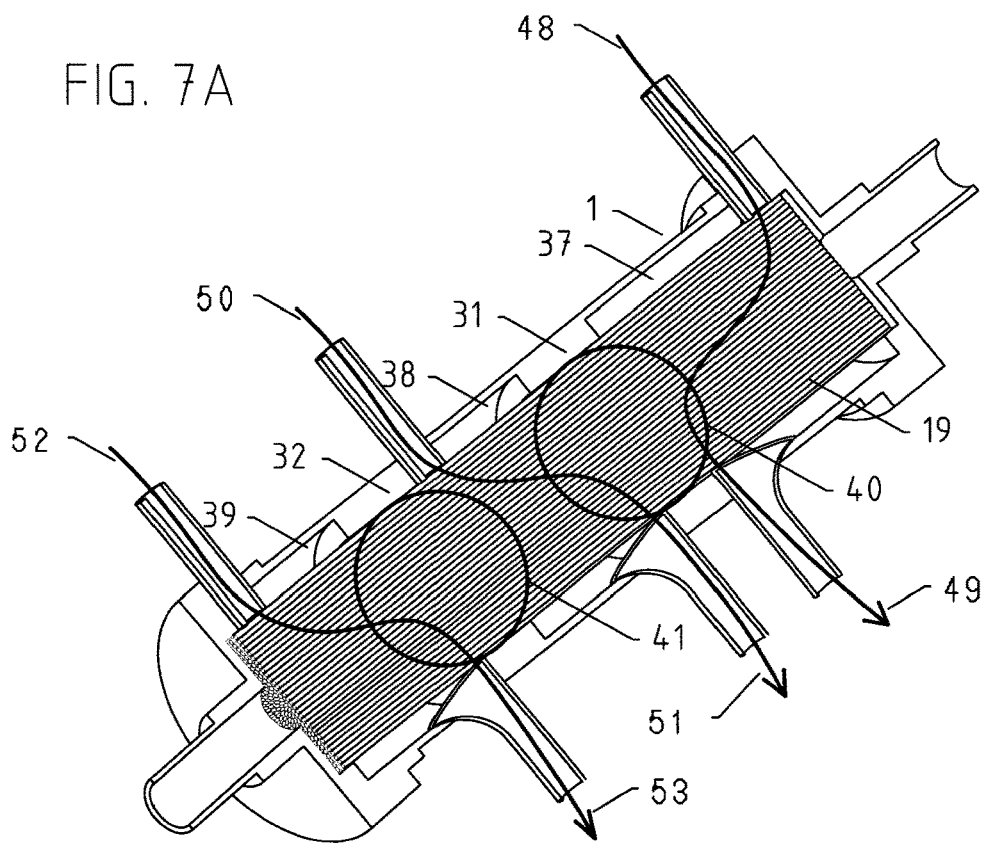
FIG. 7 depicts a schematic illustration of a downward gradient of urea concentration of the first and second dialysates across the packed bundle of the hollow fibers of the multi-chambered hemodiafiltrator.
Figure 7B:
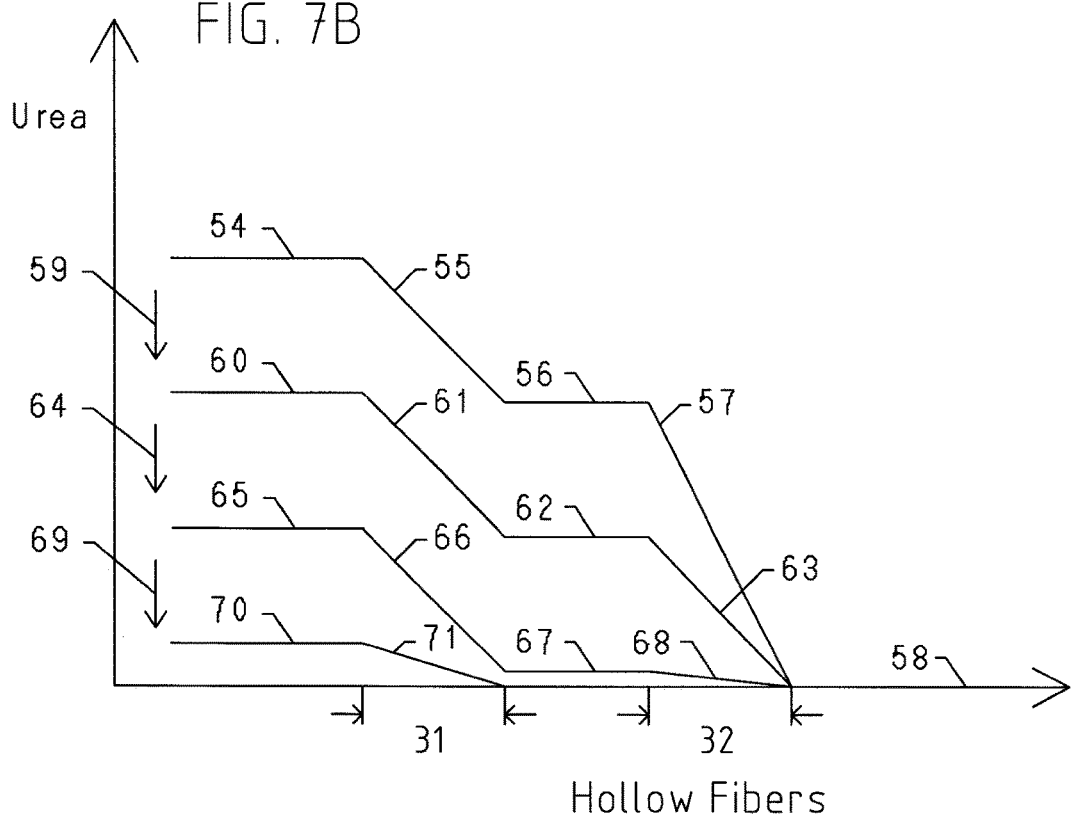

FIGS. 7A-7B show a schematic illustration of a time-dependent series of downward gradients of urea concentration of the first and second dialysates across the packed bundle of the hollow fibers of the multi-chambered hemodiafiltrator. A first dialysate 48 comprises urea that is added to a mixture of the first dialysate separately in a way concentration of the urea can be separately controlled over a session of hemodiafiltration. At start of the session of the hemodiafiltration, initial concentration of the urea would range from 20 mg/dL to 100 mg/dL, equivalent to or slightly less than a concentration of the blood urea in the patient, which then decreases along with the hemodiafiltration to a zero concentration at conclusion of the session of the hemodiafiltration. Urea concentration of a second dialysate 50 is 25% to 50% of the urea concentration in the first dialysate 48. A third dialysate 52 does not contain urea but contains ammonia at a concentration up to a normal concentration found in normal individuals (20~25 micro-mol/L). The first dialysate 48 tangentially flows through the boundary region 40 (established by the first inner circumferential divider 31) of the packed bundle of the hollow fibers 19 disposed inside the first dialysate chamber 37 and exits as a first outgoing dialysate 49. The second dialysate 50 tangentially flows through the boundary region 40 of the packed bundle of the hollow fibers 19 disposed in the second dialysate chamber 38 and exits as a second outgoing dialysate 51. Across the boundary region 40, the first dialysate 48 gets mixed mainly by diffusion over a concentration gradient of the urea between the first and second dialysates 48 and 50, with a net downward gradient in the concentration of the urea. The third dialysate 52 tangentially flows through the boundary region 41 (established by the second inner circumferential divider 32) of the packed bundle of the hollow fibers disposed in the third dialysate chamber 39 and exits as a third outgoing dialysate 53. Similar to the boundary region 40, the third dialysate 52 gets mixed mainly by diffusion over a concentration gradient of the urea between the second and third dialysates 50 and 52 across the boundary region 41, with a net downward gradient in the concentration of the urea.

Shown in FIGS. 7A-7B, an initial concentration of the urea 54 of the first dialysate 48 at the start of the session of the hemodiafiltration decreases as a linear downward gradient 55 across the boundary region 40 to a concentration 56 of the urea of the second dialysate 50. The concentration of the urea 56 of the second dialysate 50 then decreases as a linear downward gradient 57 across the boundary region 41 to a zero concentration 58 of the urea of the third dialysate 52. After a certain period of time 59 from the start of the hemodiafiltration, an hour for an example, the concentration of the urea of the first dialysate 48 drops to 60 which decreases as a linear downward gradient 61 across the boundary region 40 to a concentration 62 of the urea of the second dialysate 50. The concentration of the urea 62 of the second dialysate 50 then decreases as a linear downward gradient 63 across the boundary region 41 to the zero concentration 58 of the urea of the third dialysate 52. Similarly, after another period of time 64 from the start of the hemodiafiltration, two hours for an example, the concentration of the urea of the first dialysate 48 drops to 65 which decreases as a linear downward gradient 66 across the boundary region 40 to a concentration 67 of the urea of the second dialysate 50. The concentration of the urea 67 of the second dialysate 50 then decreases as a linear downward gradient 68 across the boundary region 41 to the zero concentration 58 of the urea of the third dialysate 52. Some time 69 prior to the conclusion of the session of the hemodiafiltration, the concentration of the urea of the first dialysate 48 drops to 70 which decreases as a linear downward gradient 71 across the boundary region 40 to a zero concentration of the urea of the second dialysate 50.

Figure 8:
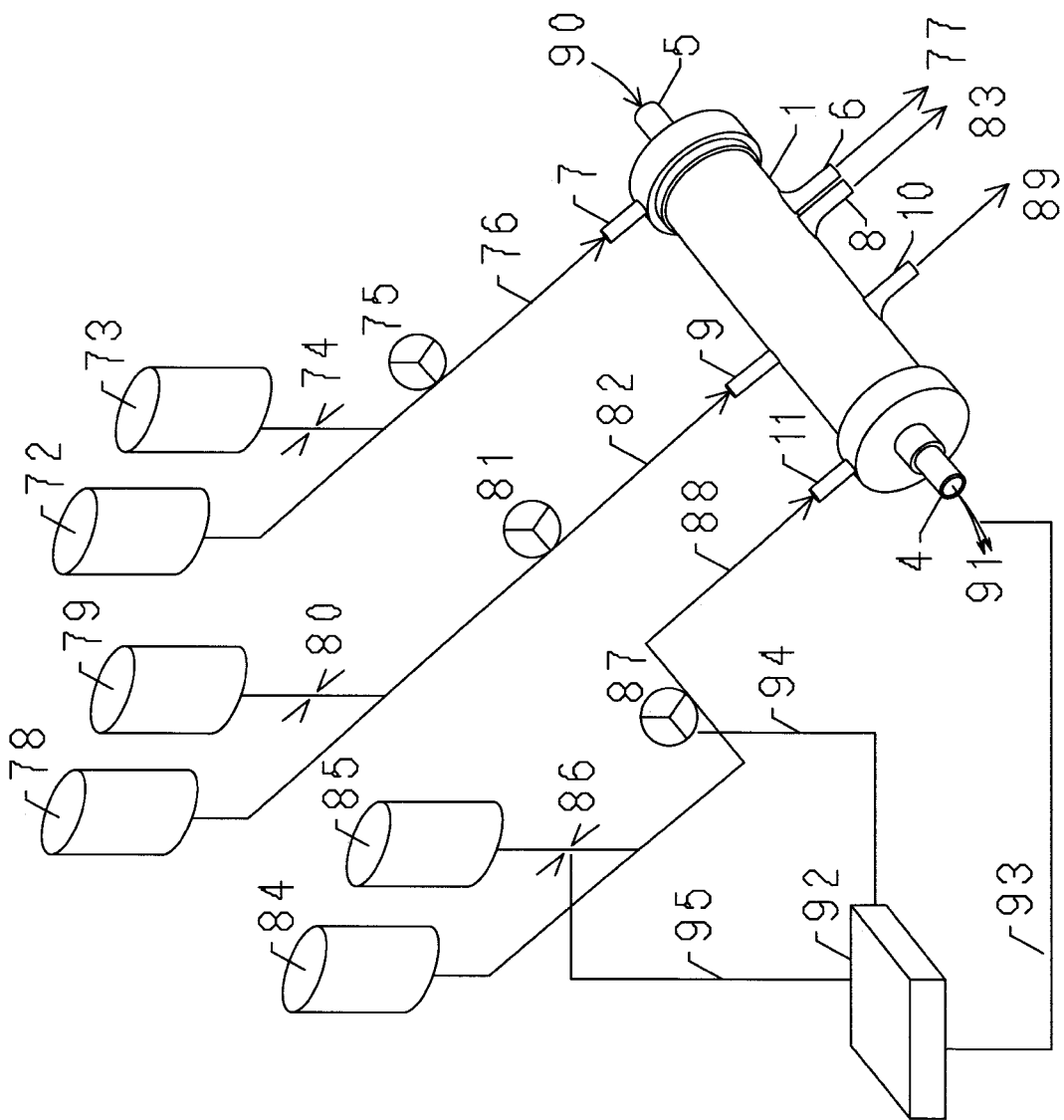
FIG. 8 shows a schematic illustration of a hemodiafiltration system of the gradient dialysate hemodiafiltration connected to the multi-chambered hemodiafiltrator and monitored by an electronic central command module.

FIG. 8 shows a schematic illustration of a gradient dialysate hemodiafiltration system, comprising a first dialysate vessel 72 connected to a first urea vessel 73 in a Y configuration. The first dialysate 76 therefore is a mixture of the first dialysate from the first dialysate vessel 72 with a first urea in the first urea vessel 73. The first dialysate 76 is configured to flow into the dialysate tubular cylinder 1 through the first dialysate intake tube 7 and to be drained out as a first wasted dialysate 77 through the first dialysate output tube 6. Volume and speed of infusion of the first urea from the first urea vessel are controlled by an infusion control 74. Volume and speed of infusion of the first dialysate 76 is controlled by a first infusion pump 75. The second dialysate 82 is a mixture of the second dialysate from the second dialysate vessel 78 and a second urea from a second urea vessel 79. The second dialysate vessel 78 is connected to the second urea vessel 79 in a Y configuration. The second dialysate 82 is configured to flow into the dialysate tubular cylinder 1 through the second dialysate intake tube 9 and to be drained out as a second wasted dialysate 83 through the second dialysate output tube 8. Volume and speed of infusion of the second urea from the second urea vessel are controlled by an infusion control 80. Volume and speed of infusion of the second dialysate 82 is controlled by a second infusion pump 81. The last dialysate 88 is a mixture of the last dialysate from the last dialysate vessel 84 and an ammonia vessel 85. The last dialysate vessel 84 is connected to the ammonia vessel 85 in a Y configuration. The last dialysate 88 is configured to flow into the dialysate tubular cylinder 1 through the last dialysate intake tube 11 and to be drained out as a last wasted dialysate 89 through the last dialysate output tube 10. Volume and speed of infusion of the ammonia from the ammonia vessel are controlled by an infusion control 86. Volume and speed of infusion of the last dialysate 88 is controlled by a third infusion pump 87.

All of the controls for the infusion of the dialysates, the urea and the ammonia in solution are centrally coordinated by an electronic command control module 92. An outgoing blood 91 from the blood output tube 4 to a patient is monitored for a series of pH, electrolytes such as potassium and bicarbonate, urea concentration and ammonia concentration at a regular interval during the session of the hemodiafiltration. Shown schematically for an illustration purpose, data of the series of values of the pH, the electrolytes, and the ammonia concentration are fed in a feedback loop 93 into the electronic command control module 92 which then electronically modulates volume and speed of the infusion of the last dialysate (94) by controlling the third infusion pump 87, and the ammonia in solution (95) by controlling the infusion control 86 to the last dialysate chamber of the multi-chambered hemodiafiltrator. Similarly, the electronic command control module 92 controls the volume and the speed of the infusion of the first and second dialysates 76 and 82, respectively, and controls the first and second urea infusion controls 74 and 80, respectively, based on the data of values of the pH, the electrolytes, and the urea of the outgoing blood 91. An incoming blood 90 through the blood intake tube 5 is not monitored by the electronic command control module 92 for pH, electrolytes such as potassium and bicarbonate, urea concentration and ammonia concentration.

It is to be understood that the aforementioned description of the gradient dialysate hemodiafiltration is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. A method for gradient dialysate hemodiafiltration for enhancing removal of protein bound uremic toxins from blood, comprising:

during hemodiafiltration, acidifying a blood of a patient in proximal and mid portions of a packed bundle of hollow fibers for blood flow of a multi-chambered hemodiafiltrator with first and second dialysates having acidic pHs, respectively, followed by normalizing a pH of the blood in a distal portion of the packed bundle of the hollow fibers with a third dialysate having a basic pH prior to sending the blood from the distal portion of the packed bundle of the hollow fibers to the patient;

during the hemodiafiltration, maintaining a urea concentration in the blood in the proximal and mid portions of the packed bundle of the hollow fibers by adding urea in a range of concentrations to the first and second dialysates for the proximal and mid portions of the packed bundle of the hollow fibers, respectively;

wherein the concentrations of the urea in the first and second dialysates phase out to zero over time during a session of the hemodiafiltration;

during the hemodiafiltration, providing the blood in the distal portion of the packed bundle of the hollow fibers with ammonia in solution at a concentration by adding the ammonia in solution to the third dialysate.

2. The method for gradient dialysate hemodiafiltration for enhancing removal of protein bound uremic toxins from blood according to claim 1, further comprising:

flowing in and draining out the first dialysate to and from, respectively, a first compartmentalized tubular dialysate chamber of the multi-chambered hemodiafiltrator;

wherein a pH of the first dialysate ranges from 5.5 to 7.0;

flowing in and draining out the second dialysate to and from, respectively, a second compartmentalized tubular dialysate chamber of the multi-chambered hemodiafiltrator;

wherein a pH of the second dialysate ranges from 6.0 to 7.5; and flowing in and draining out the third dialysate to and from, respectively, a third compartmentalized tubular dialysate chamber of the multi-chambered hemodiafiltrator;

wherein a pH of the third dialysate ranges from 7.5 to 9.5.

3. The method for gradient dialysate hemodiafiltration for enhancing removal of protein bound uremic toxins from blood according to claim 2, further comprising:

the first, second and third dialysates concurrently flow into the first, second and third compartmentalized tubular dialysate chambers, respectively; and the first, second and third dialysates concurrently drain out from the first, second and third compartmentalized tubular dialysate chambers, respectively.

4. The method for gradient dialysate hemodiafiltration for enhancing removal of protein bound uremic toxins from blood according to claim 2, further comprising:

establishing a first non-discontinuous upward pH gradient between the pH of the first dialysate in the first compartmentalized tubular dialysate chamber and the pH of the second dialysate in the second compartmentalized tubular dialysate chamber by concurrently flowing in the first and second dialysates into the first and second compartmentalized tubular dialysate chambers, respectively;

wherein the first dialysate diffuses to the second dialysate, and vice versa, through a first interfibrillar space of individual hollow fibers of a first portion of the packed bundle of the hollow fibers;

wherein an outer peripheral layer of the first portion of the packed bundle of the hollow fibers is tightly encircled by a first inner circumferential divider; and wherein the diffusion between the first dialysate and the second dialysate through the first interfibrillar space generates the first non-discontinuous upward pH gradient.

5. The method for gradient dialysate hemodiafiltration for enhancing removal of protein bound uremic toxins from blood according to claim 2, further comprising:

establishing a second non-discontinuous upward pH gradient between the pH of the second dialysate in the second compartmentalized tubular dialysate chamber and the pH of the third dialysate in the third compartmentalized tubular dialysate chamber by concurrently flowing in the second and third dialysates into the second and third compartmentalized tubular dialysate chambers, respectively;

wherein the second dialysate diffuses to the third dialysate, and vice versa, through a second interfibrillar space of the individual hollow fibers of a second portion of the packed bundle of the hollow fibers;

wherein an outer peripheral layer of the second portion of the packed bundle of the hollow fibers is tightly encircled by a second inner circumferential divider; and wherein the diffusion between the second dialysate and the third dialysate through the second interfibrillar space generates the second non-discontinuous upward pH gradient.

6. The method for gradient dialysate hemodiafiltration for enhancing removal of protein bound uremic toxins from blood according to claim 1, further comprising:

adding urea at a concentration to the first dialysate before the first dialysate flows in the first compartmentalized tubular dialysate chamber;

wherein the concentration of the urea for the first dialysate is equivalent to or less than a concentration of blood urea nitrogen of the patient for the hemodiafiltration; and adding the urea at a concentration to the second dialysate before the second dialysate flows in the second compartmentalized tubular dialysate chamber;

wherein the concentration of the urea added to the second dialysate is lower than the concentration of the urea added to the first dialysate.

7. The method for gradient dialysate hemodiafiltration for enhancing removal of protein bound uremic toxins from blood according to claim 1, further comprising:

decreasing the concentration of the urea for the first dialysate from an initial urea concentration at start of the hemodiafiltration over time to a zero urea concentration prior to conclusion of the hemodiafiltration; and decreasing the concentration of the urea for the second dialysate from an initial urea concentration at the start of the hemodiafiltration over time to the zero urea concentration prior to the conclusion of the hemodiafiltration.

8. The method for gradient dialysate hemodiafiltration for enhancing removal of protein bound uremic toxins from blood according to claim 6, further comprising:

establishing a first non-discontinuous downward gradient in the concentration of the urea between the first dialysate in the first compartmentalized tubular dialysate chamber and the second dialysate in the second compartmentalized tubular dialysate chamber by concurrently flowing in the first and second dialysates into the first and second compartmentalized tubular dialysate chambers, respectively;

wherein the first dialysate diffuses to the second dialysate, and vice versa, through the first interfibrillar space of the individual hollow fibers of the first portion of the packed bundle of the hollow fibers; and wherein the diffusion between the first dialysate and the second dialysate through the first interfibrillar space generates the first non-discontinuous downward gradient in the concentration of the urea.

9. The method for gradient dialysate hemodiafiltration for enhancing removal of protein bound uremic toxins from blood according to claim 6, further comprising:

establishing a second non-discontinuous downward gradient in the concentration of the urea between the second dialysate in the second compartmentalized tubular dialysate chamber and the third dialysate in the third compartmentalized tubular dialysate chamber by concurrently flowing in the second and third dialysates into the second and third compartmentalized tubular dialysate chambers, respectively;

wherein the second dialysate diffuses to the third dialysate, and vice versa, through the second interfibrillar space of the individual hollow fibers of the second portion of the packed bundle of the hollow fibers; and wherein the diffusion between the second dialysate and the third dialysate through the second interfibrillar space generates the second non-discontinuous downward gradient in the concentration of the urea.

10. The method for gradient dialysate hemodiafiltration for enhancing removal of protein bound uremic toxins from blood according to claim 1, further comprising:

the concentration of the ammonia in solution added to the third dialysate is up to 20~25 micro-mol/L of ammonia.

11. The method for gradient dialysate hemodiafiltration for enhancing removal of protein bound uremic toxins from blood according to claim 1, further comprising:

individually controlling and centrally coordinating infusion of each dialysate into each compartmentalized tubular dialysate chamber of the multi-chambered hemodiafiltrator by an electronic command control module;

wherein the electronic command control module individually controls and centrally coordinates the infusion of each dialysate based on a series of pH values of an outgoing blood from the distal portion of the packed bundle of the hollow fibers to the patient during the hemodiafiltration.

12. The method for gradient dialysate hemodiafiltration for enhancing removal of protein bound uremic toxins from blood according to claim 1, further comprising:

individually controlling and centrally coordinating the concentration of the urea in the first and second dialysates by the electronic command control module;

wherein the electronic command control module individually controls and centrally coordinates the concentration of the urea in the first and second dialysates based on a series of urea concentration values of the outgoing blood from the distal portion of the packed bundle of the hollow fibers to the patient during the hemodiafiltration.

13. The method for gradient dialysate hemodiafiltration for enhancing removal of protein bound uremic toxins from blood according to claim 1, further comprising:

controlling addition of the ammonia in solution to the third dialysate by the electronic command control module;

wherein the electronic command control module controls the addition of the ammonia in solution to the third dialysate based on a value of ammonia concentration of the patient's blood in vivo before the start of the hemodiafiltration.

* * * * *